United States Patent [19]

Warren

[11] 4,443,668
[45] Apr. 17, 1984

[54] EARPLUG MOUNTING DEVICE WITH AUDIO PASSAGEWAY

[76] Inventor: James C. Warren, 3808 S. Jasmine St., Denver, Colo. 80237

[21] Appl. No.: 246,445

[22] Filed: Mar. 23, 1981

[51] Int. Cl.[1] .............................................. H01M 1/05
[52] U.S. Cl. ................................ 179/156 A; 181/135; 179/156 R
[58] Field of Search ............ 179/182 R, 1 ST, 156 A, 179/157, 183, 156 R, 149, 152, 135; 181/135, 130, 131

[56] References Cited

U.S. PATENT DOCUMENTS

| | | | |
|---|---|---|---|
| 1,953,437 | 5/1934 | Schier | 181/23 |
| 2,904,640 | 9/1959 | Drener et al. | 179/156 A |
| 3,140,365 | 4/1969 | Bryant et al. | 179/156 A |
| 3,440,365 | 5/1969 | Bryant et al. | 179/156 |
| 4,179,590 | 12/1979 | Snow | 179/156 A |
| 4,311,206 | 1/1982 | Johnson | 181/135 |

FOREIGN PATENT DOCUMENTS 312358 7/1969 Sweden ........................... 179/156 A Primary Examiner—G. Z. Rubinson
Assistant Examiner—Robert Lev
Attorney, Agent, or Firm—Gary M. Polumbus

[57] ABSTRACT

An earplug mounting device for insertion into the human ear adapted to support electronic telecommunications equipment, other audio equipment or visual aids is disclosed. A main body portion of semi-rigid resilient material is insertable into the outer ear of a user and has a main body passageway therethrough. A snap connection is provided between the main body and a boom, which boom extends forwardly therefrom. A boom passageway is in air communication with the main body passageway. A pressure chamber formed along the boom passageway, with a vent providing air flow communication with the outside of the chamber, to equalize air pressure between outside air and an inner ear is provided. A receiving tube, connected to a radio receiver, is rotatably connected to the boom by a second snap connection utilizing a fitting having a third passageway in communication with the first two passageways.

12 Claims, 7 Drawing Figures

EARPLUG MOUNTING DEVICE WITH AUDIO PASSAGEWAY

BACKGROUND OF THE INVENTION

1. Field of Invention

The present invention relates to improvements in sound attenuating devices, and particularly ear insert-type devices which have the capability of supporting electronic communications devices, and other audio, as well as visual, aids.

2. Description of the Prior Art

Earplugs have been used for years to attenuate sound, but only recently have such plugs gained sophistication from a comfort and/or utilitarian standpoint. Some earplugs are now being formed to contour fit a given individual's ear and some are being incorporated into other devices such as telecommunications equipment, so that such equipment can be supported by the ear. Examples of such devices are found in my prior U.S. Pat. No. 4,223,189, issued Sept. 16, 1980.

Though many earplug or earpiece type mountings have been devised for telecommunications equipment, most of such mounting devices are constructed of relatively hard material in order to provide support for whatever gear is mounted thereon. Due to the hardness of the material, the earpiece fails to effectively dampen ambient sounds and in fact, may amplify these sounds. This shortcoming is particularly noticeable in the aviation environment, where engine and aerodynamic noise levels are a constant interference with communications. Soft material additionally provides an element of safety in the event the user encounters a blow to the head. Hard materials which can fracture, like glass, are a hazard to the user.

Another drawback of prior art mounting devices for telecommunications equipment applications, which include an earpiece that is integral with the telecommunications equipment, is that such devices cannot be used independently of the equipment, with other types of telecommunications equipment of for supporting other articles, such as eyeglasses or optical aids.

Heretofore it has not been possible to achieve a sufficiently good fit between the earpiece and the outer ear to support equipment and yet maintain comfort and dampen noise. Custom fitting, as shown in my prior U.S. Pat. No. 4,223,189, overcomes these drawbacks, but is not conducive to mass production.

Particularly when joined to telecommunications equipment through a flexible receiving tube, the prior art earpieces are often somewhat restrictive. The connection between the receiving tube and the earpiece is usually a rigid one, which under certain circumstances can interfere with the fit of the earpiece, or unduly kink or bend the receiving tube.

A related drawback to the failure of current earplug or earpiece-type mounting devices to attenuate ambient noise is associated with the fact that no standardized earplug or earpiece is currently available that has been adapted to mount telecommunications or other equipment thereto. The primary objective in the past has been light weight and comfort, not noise attenuation.

Many prior art devices are primarily of integral construction, meaning that breakage or excessive wear require replacement of the entire mounting device. The use of interchangeable parts in such a device would lower many replacement costs.

The fact that a mounting device for an ear could be disassembled would also make cleaning the actual ear insert easier as well as more practical. With an earplug mounting device that is constantly inserted and removed, hygiene is extremely important. An earplug that is easily washable, without interference from electronic devices, is extremely important.

OBJECTS AND SUMMARY OF THE INVENTION

The principal object of the present invention is to provide an earplug mounting device adapted to support electronic telecommunications equipment as well as other audio and visual aids.

A related object of the present invention is to provide an earplug mounting device that attenuates noise when used in relatively noisy environments, like those which all aircraft pilots encounter.

Another related object of the present invention is to provide an earplug mounting device that can be inexpensively mass produced.

A further object of the present invention is to provide an earplug mounting device that is capable of being connected to a radio receiver receiving tube so as to enable ease of movement of the head of the user.

Still a further object of the present invention is to provide an earplug mounting device that can be easily disassembled into component parts for easy replacement and cleaning of the component parts.

In accordance with the objects of the present invention, a semi-rigid resilient main body of an earplug mounting device is adapted to be inserted within a human being's outer ear. A main body passageway provides an air way for conducting sound to the inner ear through the main body. On an exterior side of the main body is mounted a snap ring, circumscribing the main body passageway.

A lightweight plastic boom is mounted on the main body and extends forwardly from the ear of the user toward his eyes. The boom includes an enlarged rounded end having an enlarged hole defining an air chamber at the center thereof, and a forwardly extending rectangular portion. A pin projection extends perpendicularly away from the boom on the side on which the snap is mounted. The pin projects into the main body to thereby prevent rotation of the boom relative to the main body.

On one side of the boom, to be mounted adjacent to the main body, is integrally connected a snap having a bore therethrough. The snap is adapted to be matingly received within the snap ring of the main body to thereby interconnect the main body and the boom. On a second side or exterior side of the boom is located a snap ring, integrally connected to the boom. A boom passageway is therefore established by the bore in the snap, hole in the boom and the snap ring. The air chamber is laterally intersected by a pressure equalization vent to obviate pressure differences existing between the outside and inside of the device.

A receiving tube fitting is adapted to be matingly received within the snap ring of the boom, and be connected to a receiving tube providing audio input from a radio receiver. A fitting passageway provides air communication through the fitting between the boom passageway and the receiving tube.

DESCRIPTION OF THE PREFERRED EMBODIMENT

Figure 1:
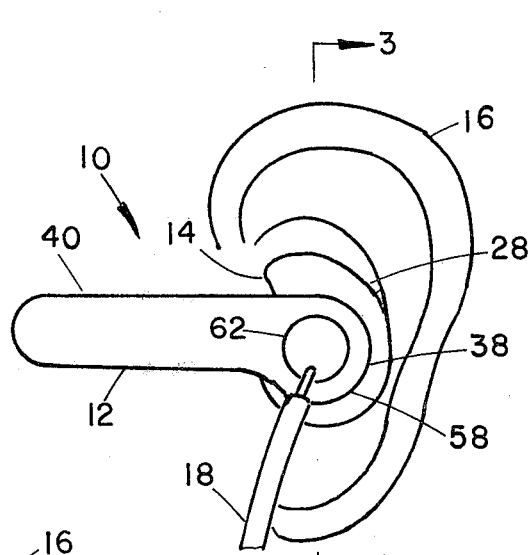
FIG. 1 is a side elevational view of the earplug mounting device of the invention mounted on the outer ear of an individual and being connected to a telecommunication receiving tube.
Figure 5:
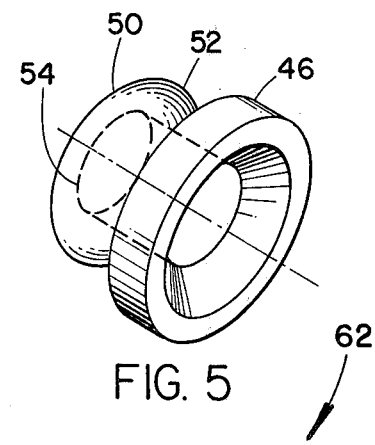
FIG. 5 is an enlarged perspective view of the receiving tube fitting of the invention shown in FIG. 1.
Figure 6:
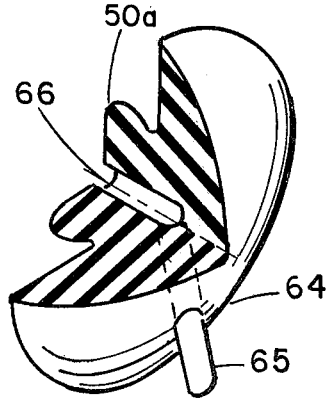
FIG. 6 is an enlarged perspective view of the main body of the invention shown in FIG. 1.

An earplug mounting device 10 onto which audio or visual aids can be mounted is seen in FIG. 1. The earplug mounting device 10 includes a boom 12 that is particularly suitable for carrying a commercially available radio microphone and receiver (not shown), and a main body portion 14 (FIG. 5) releasably connected to the boom and insertable into a human outer ear 16, so that the outer ear 16 supports the entire earplug mounting device 10 and attached equipment. The earplug mounting device carries sound waves to the ear from the radio receiver through a short flexible plastic receiving tube 18, thereby providing acoustic communication between the radio receiver and the earplug mounting device. In the preferred embodiment, the earplug mounting device therefore presents a small, lightweight, ear mounted device for carrying on two-way radio communication.

The main body 14 (FIG. 5) is similar to the type currently utilized for mounting hearing aids. The main body is available commercially in a variety of sizes different to substantially conform to the outer ear 16 of any human being. The main body 14 is made of a semi-rigid resilient material that has sound dampening or attenuating characteristics when inserted into the outer ear 16. The fit between the outer ear 16 and the main body 14 is very close, essentially sealing the outside noise and pressure from the user of the earplug mounting device 10.

The main body 14 therefore includes a generally disc-shaped earplug 20 (FIG. 2) having a first or inner side 22 and a second or outer side 24. An integral elongated extension 26 protrudes from an edge of the earplug in a generally parallel relationship to an axis through the center of and perpendicular to the sides 22 and 24 of said earplug. Approximately diametrically opposed from the extension 26 is an integral wing 28 extending in the same direction as the extension away from the earplug.

The extension 26 and wing 28 are located on the first or inner side 22 of the main body 14, which side 22 is adapted to fit adjacent to the surface of the outer ear 16. The extension is insertable into a portion of an auditory canal 30 (FIG. 3) of the human ear in a substantially airtight relationship. The second side includes a pin hole 70 which assists in preventing relative rotation between the boom 12 and main body 14, in a manner to be described hereinafter.

The main body 14 is therefore releasably mounted in the ear by the insertion of the integral wing 28 and the extension 26 into the outer ear 16. The integral wing 28 protrudes into a rear cavity of the outer ear, while the extension protrudes into the opening from the outer ear to the auditory canal 30. When a proper fit of the standardized main body 14 is achieved, the fit of the wing and the extension slightly flex the earplug 20, which in turn biases the wing and the extension against their respective portions of the outer ear.

The extension 26 includes along the length thereof a bore 32, which bore 32 assists in the conveyance of sound to the auditory canal 30 by providing an airway along which sound waves can travel. The bore 32 terminates near the generally flat second or outer side 24 (FIG. 2) of the main body, which outer side 24 forms an exterior surface of the main body. A counterbore 34, of relatively large diameter as compared to the bore 32, is formed or drilled from the outer side to intersect the bore 32. A round snap ring 44 having an opening therein is rigidly connected to the main body 14 within the counterbore 34 for purposes of connecting the boom 12 to the main body, which connection will be discussed in detail hereinafter. A main body passageway 36 is thereby established by the bore 32, counterbore 34 and snap ring 44, providing an airway on which sound waves can travel.

The boom 12 is of generally flat key-shaped configuration (FIG. 1), having a relatively large rounded end 38 and an integral rectangular portion 40 of rectangular transverse cross section extending away from the rounded end. When the boom is connected to the main body 14, in a manner to be described shortly, the rectangular portion 40 extends from the outer ear 16 toward the eyes of a user. A hole 42 (FIG. 2) is drilled or formed in the rounded end at approximately the center of a circle defined by the rounded end 38, which hole is aligned with the bore 32 and counterbore 34 of the main body 14 upon connection of the boom 12 thereto.

Figure 4:
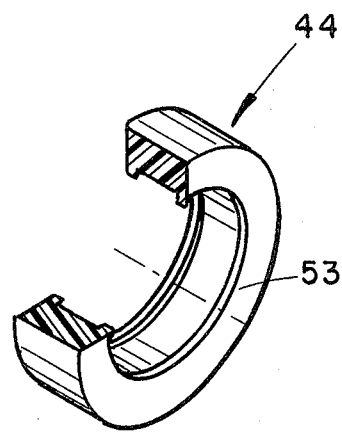
FIG. 4 is an enlarged fragmentary perspective view of the snap ring of the invention shown in FIG. 1.
Figure 3:
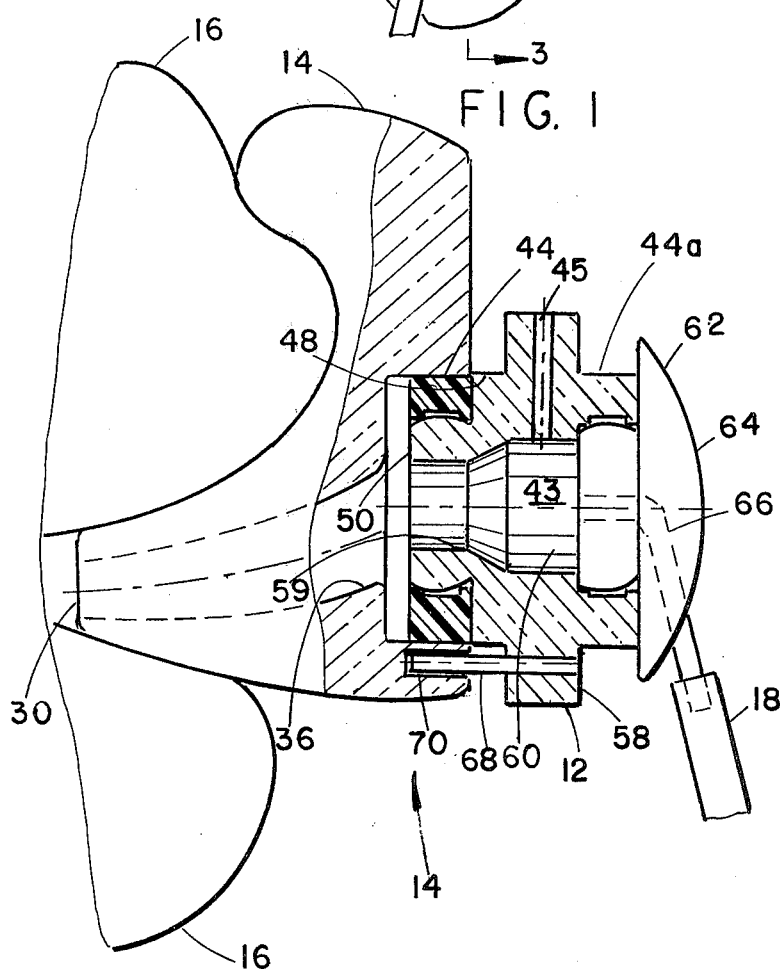
FIG. 3 is an enlarged sectional view taken in the plane of line 3—3 of FIG. 1.
Figure 2:
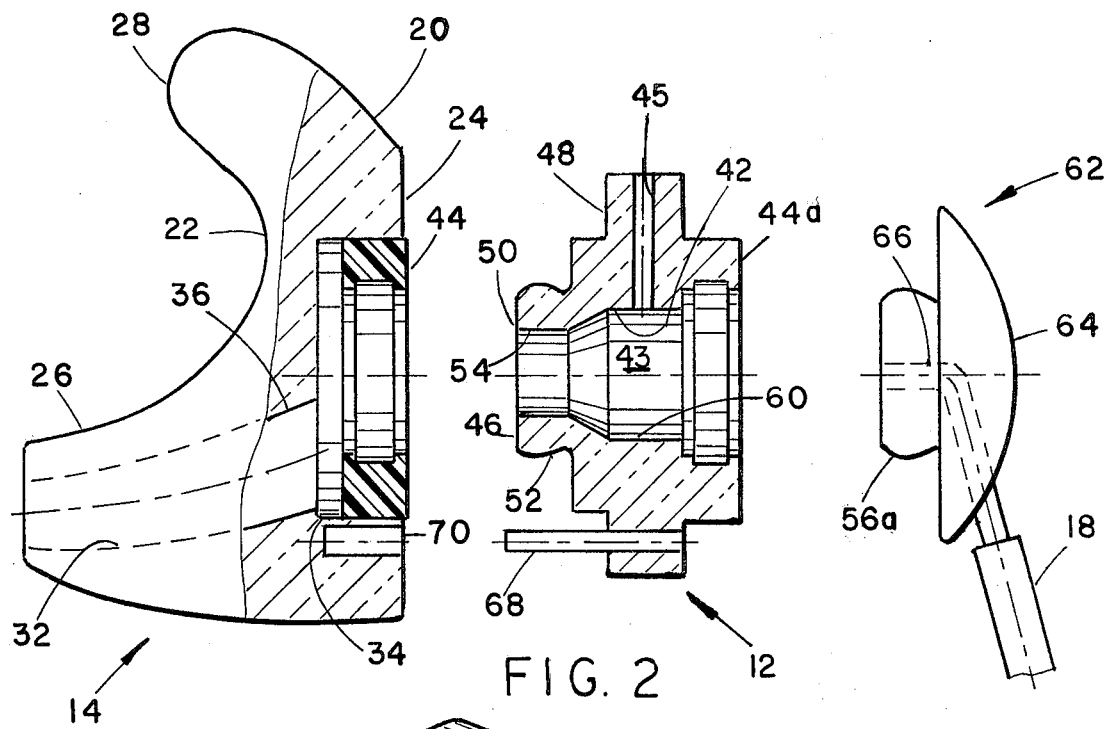
FIG. 2 is an exploded front elevational view of the invention shown in FIG. 1.
Figure 7:
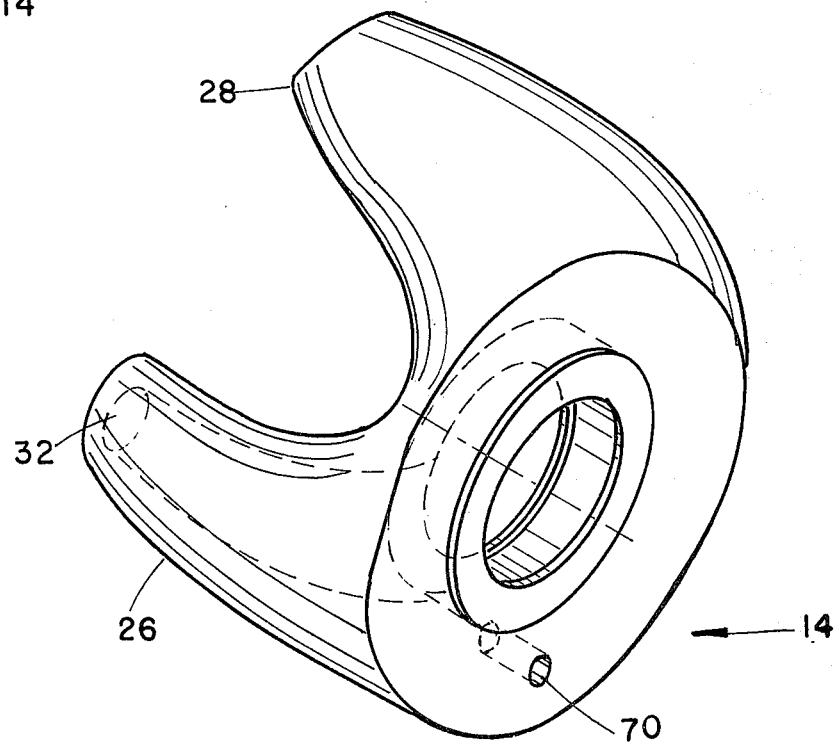

The hole 42 in the boom 12 further defines an air chamber 43 which air chamber is enlarged relative to the cross sectional areas of the bore 32 and tube 18. In order to connect the boom 12 to the main body 14, the snap ring 44 (FIG. 4) interfits the counterbore 34 of the main body 14 and is held rigidly in position flush with the flat outer side 24 (FIGS. 2 and 3). The snap ring 44 is engaged by a snap or nipple 46 (FIG. 2) integrally connected to one side 48 of the rounded end 38 of the boom. A top 50 of the snap 46 is of toroidal or doughnut shape, supported at a raised position above the rounded end of the boom by an integral diverging, generally frustoconically-shaped shoulder 52 (FIG. 2). The top 50 of the snap 46 is received between a pair of circumferential ribs 53 in the snap ring 44 (FIG. 4).

The snap 46 continues to provide an airway, and therefore supports sound waves, by having a bore 54 therethrough coaxial with the hole 42 and the counterbore 34 of the main body 14, when the nipple 46 is snapped into the snap ring 44.

A second side 58 of the rounded end 38 of the boom 12 has a second snap ring 44A integrally molded thereon, again coaxial with the hole 42 in the rounded end 38. The hole 42 of the boom 12, the air chamber 43, the bore 54 in the snap 46 and the second snap ring 44A provide a boom passageway 60 (FIGS. 2 and 3), again forming an airway through the boom for carrying sound waves.

The air chamber 43 extends the entire width of the boom between the sides 48 and 58 and is laterally intersected by a pressure equalization vent 45. The vent 45 is in air communication with the ambient air in which the mounting device 10 is utilized. In an airplane, a sudden pressure differential between the inner ear and the exterior air, which would normally result in expanding pressure in the inner ear against the main body 14 and resulting pain or damage to the user, is equalized without pain and with considerably less risk of damage.

The second side 58 of the boom 12 also has connected thereto a pin 68 adapted to project into the pin hole 70 in the main body 14 (FIGS. 2 and 3). The pin is located a set distance away from the potential axis of rotation of the boom 12 about the main body 14.

A receiving tube fitting 62 (FIG. 5) interconnects the boom passageway 60 with the flexible receiving tube 18. The fitting 62 is of similar construction to the snap 46 at the one side 48 of the boom 12. A top 50A of the fitting 62 engages the second snap ring 44A in a manner identical to the connection between the snap 46 and snap ring 44 connecting the boom 12 to the main body 14, previously described. A semi-spherical base 64 of the fitting 62 is positioned adjacent to the second side 58 of the boom 12, when the fitting is connected to the boom. A fitting passageway 66 is formed all the way from the top 50A through the spherical base 64 providing air communication from the receiving tube 18 to the boom passageway 60. The fitting passageway 66 is of smaller cross sectional area than the air chamber 43 into which the passageway 66 communicates. A hollow stem 65 extends away from the fitting passageway 66 to connect to the receiving tube 18.

It is therefore appreciated that when the receiving tube 18 is joined to a radio receiver in a conventional manner, air, and therefore sound transmission, can be maintained from the receiver through the receiving tube to the fitting passageway 66. The fitting passageway 66 is in continuous communication with the boom passageway 60, and the boom passageway 60 is in further continuous communication with the main body passageway 36, when the earplug mounting device 10 is fully assembled (FIG. 3), as has been described. Lastly, the main body passageway 36 provides an airway to the auditory canal 30 of the ear, allowing the radio communication to be directed to the auditory sensing system of the individual.

The receiving tube fitting top 50A, and its connection to the second snap ring 44A, allows the receiving tube 18 to rotate relative to the boom 12 about the snap connection between the fitting 62 and the boom 12. This rotation is in fact a desirable characteristic of the earplug mounting device 10. Though the earplug mounting device 10 is snugly fit within the outer ear 16, it can be jarred loose by external forces. Therefore, any feature of the earplug mounting device tending to reduce those external forces helps insure a better and longer lasting conformable fit between the earplug mounting device 10 and the ear. Because of the relative rotation provided by the fitting 62 between the receiving tube 18 and the boom 12, the user of the earplug mounting device, in an electronic telecommunication situation as described, can easily adjust the positioning of the tube 18 relative to the boom 12.

The connection between the main body 14 and the boom 12, and the connection between the boom 12 and receiving tube 18, are both selective in that, when desired by the user, those connections may be broken. The connections are basically snap connections that are easily separated. This feature of the earplug mounting device 10 permits easy disassembly into the primary component parts of the earplug mounting device, main body 14, boom 12 and receiving tube fitting 62. Should any of these parts wear out or break, the component part can be replaced without replacing the entire earplug mounting device. Furthermore, the earplug mounting device can be readily cleaned, particularly the main body 14. The fact that the main body extension 26 is insertable within a portion of the auditory canal 30 of the ear, necessitates, in some individuals more than others, that wax will be encountered. It is therefore desirable to periodically clean the main body portion of the earplug mounting device. This aspect of the invention also is desirable when it is understood that situations, particularly those encountered by commercial aircraft pilots, may require that one earplug mounting device be transferred between pilots.

The fact that the main body 14 of the earplug mounting device 10 is commercially available in several standard styles allows the earplug mounting device to be relatively easily adapted to mass production and easy part replacement. Such main bodies are available in sufficient different sizes so that virtually any person can obtain a fit generally conformable to his or her particular outer ear 16.

Again with reference to the commercial, or private, aircraft environment, dampening extraneous noise from any aircraft engines and aerodynamic forces is extremely desirable, both from an efficiency as well as a safety point of view. Incorporation into the earplug mounting device 10 of technology already developed in hearing aids, specifically the majority of the construction of the main body 14, assists this particular innovation of the present invention greatly. As with the earplug mounting device 10, in a hearing aid it is important that the amplified sounds of the hearing aid reach the area of the inner ear. In the earplug mounting device, the sound waves carried from a radio receiver must be directed to the same area, without being distorted or garbled by other noises commonly existing in an aircraft cockpit.

Therefore, although the present invention has been described with a certain degree of particularity, it is understood that the present disclosure has been made by way of example and that changes in details of structure may be made without departing from the spirit thereof.

It is claimed:

1. An earplug mounting device for insertion into the human ear, said mounting device adapted to support audio aids and provide sound communication between a radio receiver and the human ear, wherein the human ear includes an outer ear and an auditory canal leading to an inner ear, said earplug mounting device and radio receiver comprising in combination:
   a resilient semi-rigid main body mountable in the outer ear, said main body having a main body passageway therethrough;
   a support boom onto which an audio aid can be attached which is releasably connected to said main body so as to be fixedly positioned relative to said main body, said boom having a boom passageway therethrough in acoustic communication with said main body passageway; and
   a flexible tube defining an air passageway for carrying sound waves, one end of said tube releasably connected to said boom at said boom passageway, said flexible tube being operably connected at another end to said radio receiver, said flexible tube being in acoustic communication with said boom passageway and said radio receiver whereby sound waves emanating from said radio receiver can be carried through the tube, boom and main body into the auditory canal of an individual utilizing the device.

2. The invention defined in claim 1 wherein said boom is releasably connected to said main body by first snap connection means.

3. The invention defined in claim 1 wherein said flexible tube is rotatably connected to said boom by second snap connection means.

4. The invention defined in claim 3 wherein said second snap connection means includes:
a generally spherically-shaped snap and a snap ring adapted to receive said snap.

5. The invention defined in claim 2 wherein said first snap connection means includes:
a generally spherically-shaped snap and a snap ring adapted to receive said snap.

6. The invention defined in claim 3 wherein said snap of said second snap connection means further includes:
a tube fitting adapted to be matingly received in said second snap, said fitting adapted to connect to said flexible tube in a sealed acoustic communicative relationship, said fitting further having a fitting passageway therethrough providing acoustic communication between said tube and said boom passageway.

7. The invention defined in claim 5 wherein said tube fitting further includes:
a top of generally spherical shape supported at a preselected distance above a generally toroidally-shaped base by a diverging truncated cone-shaped shoulder.

8. The invention as defined in claim 1 wherein said support boom has a rounded portion and a rectangular portion of rectangular transverse cross section extending away from said rounded portion onto which rectangular portion said radio microphone is attached, said rounded portion being releasably connected to said main body so as to be fixedly positioned relative to said main body, said rounded portion having said boom passageway therethrough in acoustic communication with said main body passageway.

9. An aircraft pilot earplug mounting device for insertion into the human ear, said earplug mounting device adapted to support a radio microphone and provide sound communication between a radio receiver and the human ear, wherein the human ear includes an outer ear and an auditory canal leading to an inner ear, said earplug mounting device comprising in combination:
a resilient semi-rigid sound attenuating main body mountable in an essentially sealed fit against the outer ear, said main body having a main body passageway therethrough;
a support boom onto which a radio microphone can be attached is releasably connected to said main body so as to be fixedly positioned relative to said main body, said boom having a boom passageway therethrough in acoustic communication with said main body passageway, said boom further having vent means formed therein for providing acoustic communication between said boom passageway and the ambient air; and
a flexible tube defining an air passageway for carrying sound waves, one end of said tube releasably connected to said boom at said boom passageway, said flexible tube being operably connected at another end to said radio receiver, said flexible tube being in acoustic communication with said boom passageway and said radio receiver whereby sound waves emanating from said radio receiver can be carried through the tube, boom and main body into the auditory canal of an individual utilizing the device.

10. The invention as defined in claim 9 wherein said boom passageway includes an air chamber or relatively enlarged cross section compared to the air passageway of said flexible tube and the main body passageway of said main body.

11. An earplug mounting device for insertion into the human ear, said mounting device adapted to support audio aids and provide sound communication between a radio receiver and the human ear, wherein the human ear includes an outer ear and an auditory canal leading to an inner ear, said earplug mounting device and radio receiver comprising in combination:
a resilient semi-rigid main body mountable in the outer ear, said main body having a main body passageway therethrough;
a generalized support boom onto which any one of a number of different types of audio aids can be attached which is releasably connected to said main body so as to be fixedly positioned relative to said main body, said boom having a boom passageway therethrough in acoustic communication with said main body passageway; and
a flexible tube defining an air passageway for carrying sound waves, one end of said tube releasably connected to said boom at said boom passageway, said flexible tube being operably connected at another end to said radio receiver, said flexible tube being in acoustic communication with said boom passageway and said radio receiver whereby sound waves emanating from said radio receiver can be carried through the tube, boom and main body into the auditory canal of an individual utilizing the device.

12. An earplug mounting device for insertion into the human ear, said mounting device adapted to support audio aids and provide sound communication between a radio receiver and the human ear, wherein the human ear includes an outer ear and an auditory canal leading to an inner ear, said earplug mounting device and radio receiver comprising in combination:
a resilient semi-rigid main body mountable in and essentially sealed against the outer ear, said main body having a main body passageway therethrough;
a support boom onto which an audio aid can be attached which is releasably connected to said main body so as to be fixedly positioned relative to said main body, said boom having a boom passageway therethrough in acoustic communication with said main body passageway; and
a flexible tube defining an air passageway for carrying sound waves, one end of said tube releasably connected to said boom at said boom passageway, said flexible tube being operably connected at another end to said radio receiver, said flexible tube being in acoustic communication with said boom passageway and said radio receiver whereby sound waves emanating from said radio receiver can be carried through the tube, boom and main body into the auditory canal of an individual utilizing the device.

* * * * *